US00PP08764P

United States Patent [19]

Mantel

[11] Patent Number: Plant 8,764

[45] Date of Patent: May 31, 1994

[54] LILY PLANT LILIUM 'RED DWARF'

[76] Inventor: Homme Mantel, 15361 SE. Bluff Rd., Sandy, Oreg. 97055

[21] Appl. No.: 100,480

[22] Filed: Jul. 30, 1993

[51] Int. Cl.[5] ..... A01H 5/00

[52] U.S. Cl. ..... Plt./87.4

[58] Field of Search ..... Plt. 87.4

[56] Reference Cited

U.S. PATENT DOCUMENT

PLT 6660 3/1989 McRae ..... PLT/87.4

*Primary Examiner*—David T. Fox

[57] ABSTRACT

A new variety of hybrid lily plant bearing large upfacing to slightly outfacing flowers of excellent form and long persistence. The new hybrid is particularly characterized by a short, sturdy stem and by flowers of vibrant unspotted deep red color with clawed tepals and lightly ruffled outer tepal margins. This combination is completely new in the Asiatic hybrid divisions of lilies suited to forcing and to mass commercial cultivation. The variety is highly resistant to fusarium disease and shows tolerance of virus. The bulbs may be precooled and forced into flower under glass out of season. The clone is vigorous and is a good grower and propagator.

1 Drawing Sheet

BACKGROUND OF THE INVENTION

My new variety of lily plant originated as a seedling, which first flowered in 't Zand, Netherlands in 1986. The breeding efforts had as their objective the production of shorter Asiatic hybrid lilies with deep red buds and flowers, suited to forcing into flower out of season, heretofore unknown in the lily breeding art.

I achieved the desired objective by intercrossing Lilium 'Charisma' (U.S. Plant Pat. No. 4,180) with Lilium 'Red Carpet' (unpatented). The buds and flowers of my new lily are characterized by an upfacing to slightly outfacing orientation, large size, and a deep red color. The clone possesses unusually short, strong, stout stems. In addition, the clone possesses to a high degree desirable characteristics of hybrid vigor. The clone is a good grower and propagator, as observed at 't Zand, Netherlands.

My new variety of lily plant has been asexually reproduced by me and under my direction at 't Zand, Netherlands. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

The most closely related plant known to myself is a sibling plant from the same cross named 'Scarlet Dwarf'. This sibling is the subject of a copending application. While 'Red Dwarf' and 'Scarlet Dwarf' are similar in size, plant confirmation and flower characteristics, they are easily distinguished by the fact that the ovaries of 'Red Dwarf' are inconspicuous and nearly the red color of the tepals, while those of 'Scarlet Dwarf' are much more conspicuous, being near straw color even when grown under cool or intensely illuminated conditions. Moreover, both the inner and outer tepals of 'Scarlet Dwarf' are slightly ruffled by marginal undulations, while such undulations are virtually confined to the inner tepals of 'Red Dwarf' and appear only on flowers that have been open for several days. The tepals of 'Red Dwarf' are less stiff, causing them to reflex more at the tips than those of 'Scarlet Dwarf'. The flowers of 'Red Dwarf' are noticeably flatter than those of 'Scarlet Dwarf'.

DESCRIPTION OF THE DRAWING

My new variety of lily plant is illustrated in the accompanying photographic drawing, which shows the open bloom in full color and illustrates the flower form, the tepal arrangement, and in particular the novel and distinctive upfacing to slightly outfacing deep red flowers with clawed tepals and lightly ruffled outer tepal margins, the deep red slightly more outfacing buds, and the short, sturdy stem.

DESCRIPTION OF THE NEW VARIETY

The following is a detailed description of my new variety of Asiatic hybrid lily, with nomenclature according to the *International Lily Register* (The Royal Horticultural Society of London, Second Edition, 1969), and with color designations according to the Colour Chart of The Royal Horticultural Society, published by the Society in 1966.

The Plant

Origin: Seedling.

*Seed parent.*—Lilium 'Charisma'.

*Pollen parent.*—Lilium 'Red Carpet'.

Commercial classification: Hybrid Lilium clone.

Horticultural classification: Division IA, Upright Asiatic hybrid lily, according to the Horticultural Classification of Lilies, The Royal Horticultural Society of London Form: Single stem, erect and stately.

Height: 50 to 70 cm from bulbs 14 to 18 cm in circumference, provided their light levels are adequate; low light levels may cause "stretching."

Internode length: Normally close to 3–6 mm at mid-stem. Forcing of the bulbs under glass after prolonged cold storage may produce shorter than typical stems with internodes as short as 1–2 mm at mid-stem. Forcing of very densely planted bulbs under glass with low light levels may cause atypically stretched stems with elongated internodes of 7–8 mm at mid-stem.

Growth: Vigorous and upright.

Foliage quantity: Abundant.

Size of leaf: 8 to 12 cm long × 1.5–2.5 cm wide.

Shape of leaf: Lanceolate (pointed).

Texture: Leathery and glossy.

Color: Medium to dark green, lighter on lower side.

Bulb size: Any size, ranging to 25 cm circumference commercially.

Bulb color: White, with flushes of pink or yellow after exposure to light.

The Bud

Form: Obtuse, ovoid, and long.

Size: 7 to 9 cm long and 8 to 12 cm in circumference just prior to opening.

Opening: Bud opens slowly, in response to morning light; this takes about one hour.

Color: R.H.S. CC red 44 C to 46 D, with base and tips retaining some green coloration until just prior to opening.

Peduncle: Averages 2 to 5 cm, but it may elongate if light levels are too low or if bulbs have been improperly stored prior to forcing. Color is deep green with a deep plum overlay.

The Flower

Blooming habit: Annually in midseason; flowers once and profusely.

Size: Flowers are large-sized, averaging 15 to 17 cm in diameter, reflexing at the tips on the second day to 14 to 16 cm in diameter. The tepals are broad: outer tepals are 1.75 to 2.5 cm wide at the center, and the inner tepals are 2.25 to 3 cm wide at the center. The tepals are conspicuouly clawed; that is, they are narrow at the base only, in the area parallel to the nectaries.

Borne: In a single racemic inflorescence producing 4 to 8 flowers from a bulb 14 to 16 cm in circumference.

Shape: Flowers form an open bowl with lightly recurved tepal tips by the second day after opening. As the flower ages, the outer tepal margins become very lightly ruffled but the inner tepals remain unruffled.

Tepalage: Typical of genus Lilium, with 6 imbricated tepals.

Tepal color: R.H.S. CC red 44 B to 47 A/B, shading into 46 B at the center, depending upon growing temperatures and light levels. Flowers will become more orange-red and lighter if temperatures are too high or light levels are too low.

Tepal spotting: None.

Tepal longevity: Tepals stay on stems about three weeks.

Pedicel length: Average 5 to 10 cm long.

Pedicel color: Dark green with deep plum overlay.

Pedical form: Sturdy and horizontal to slightly ascending.

Nectaries: present on both inner and outer tepals, substantially typical of the Asiatic hybrid class, occasionally showing specks of callous near the apex of nectary channels.

Color changes: Flowers become a slightly lighter but more crimson (less orange) red as the flowers age. Low light levels and extreme heat may cause a decrease in anthocyanin levels, making the color less crimson(more orange) and less intense.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting.

The Reproductive Organs

Stamens: Arrangement typical of genus Lilium. Six stamens with R.H.S. CC red 44 D filaments 8 to 12 cm long.

Pollen and anthers (dehisced): R.H.S. CC greyed orange 172A to greyed red 178A.

Pistil: One in number, 6 to 8 cm long.

Stigma: Soft red (R.H.S. CC red 42 D), very small in size.

Characteristics of ovary: Characteristic of genus Lilium, but inconspicuous due to their color, R.H.S. red 44 B to 47 A/B, virtually the same as that of the tepals, which is distinctive when taken with remaining characteristics.

The Fruit

Fertility: The fruit bears fertile seed.

Shape: Ovoid.

Color at maturity: Soft brown, sometimes overlaid with deep plum.

My new variety of Asiatic hybrid lily most nearly resembles 'Red Carpet', but it has larger, broader-petalled flowers of greater substance and a deeper, more crimson red color. Its tepal tips do not recurve as sharply as do those of 'Red Carpet', and it has shorter pedicels. It has a shorter forcing period than does 'Red Carpet' and it remains shorter when forced.

I claim:

1. A new and distinctive variety of Asiatic hybrid lily plant substantially as herein shown and described, characterized by its high resistance to disease; its tolerance of virus; its vigorous growth and rapid natural propagation; the excellence of its flower form, size, and substance; its versatility both as a garden plant and as a pot plant produced from pre-cooled bulbs forced under glass out of season; and in particular by its unique short, sturdy stems with scarlet red buds and semi-upfacing crimson red flowers with clawed tepals, a combination unique among Asiatic hybrid lilies suited to forcing and to mass commercial cultivation.

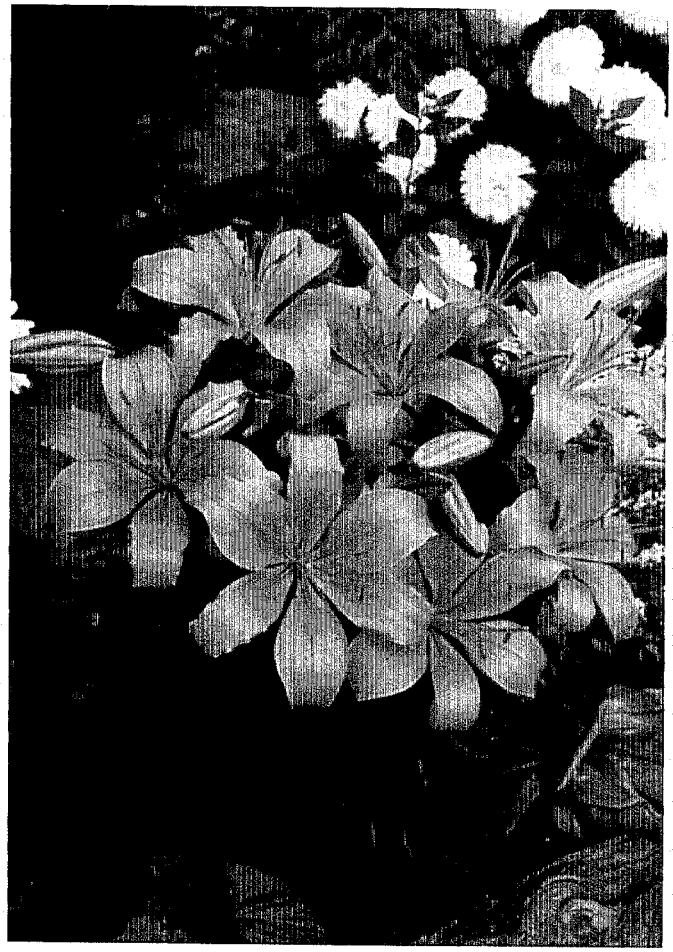

* * * * *